United States Patent [19]

Butler

[11] Patent Number: 5,196,623
[45] Date of Patent: * Mar. 23, 1993

[54] AROMATIC ALKYLATION PROCESS EMPLOYING ZEOLITE OMEGA CATALYST

[75] Inventor: James R. Butler, Houston, Tex.

[73] Assignee: Fina Technology, Inc., Dallas, Tex.

[*] Notice: The portion of the term of this patent subsequent to Dec. 17, 2008 has been disclaimed.

[21] Appl. No.: 807,698

[22] Filed: Dec. 16, 1991

Related U.S. Application Data

[63] Continuation-in-part of Ser. No. 371,502, Jun. 23, 1989, Pat. No. 5,073,653.

[51] Int. Cl.$^5$ ............................................. C07C 2/66
[52] U.S. Cl. ................................... 585/467; 585/449; 585/453
[58] Field of Search ............... 585/449, 323, 467, 475, 585/453

[56] References Cited

U.S. PATENT DOCUMENTS

| | | | |
|---|---|---|---|
| 3,551,510 | 12/1970 | Pollitzer et al. | 585/323 |
| 3,716,596 | 2/1973 | Bowes | 585/467 |
| 3,761,396 | 9/1973 | Pickert | 585/467 X |
| 4,107,224 | 8/1978 | Dwyer | 585/449 |
| 4,169,111 | 9/1979 | Wight | 585/323 |
| 4,185,040 | 1/1980 | Ward et al. | 585/467 |
| 4,241,036 | 12/1980 | Flanigen et al. | 423/328 |
| 4,301,316 | 11/1981 | Young | 585/467 X |
| 4,849,569 | 7/1989 | Smith, Jr. | 585/467 X |
| 5,003,119 | 3/1991 | Sardina et al. | 585/323 |
| 5,073,653 | 12/1991 | Butler | 585/449 |

FOREIGN PATENT DOCUMENTS

0272830 6/1988 European Pat. Off.

*Primary Examiner*—W. J. Shine
*Assistant Examiner*—Douglas J. McGinty
*Attorney, Agent, or Firm*—Joe A. Schaper

[57] ABSTRACT

A process is provided for the alkylation of aromatic substrates with a $C_2$-$C_4$ alkylating agent over an alkylation catalyst comprising zeolite omega at moderate temperature and pressure conditions to provide liquid phase conditions.

The liquid phase alkylation process is carried out using a plurality of series connected reaction stages operated at an average temperature of no more than 300° C. with the interstage injection of the $C_2$-$C_4$ alkylating agent in a manner to maintain at least 2 mole percent of alkylating agent solubilized in the aromatic substrate.

The reaction stages of a multistage system are operated at a pressure above the vapor pressure of the aromatic substrate and below the vapor pressure of the alkylating agent at the alkylation reaction conditions. The aromatic substrate and the alkylating agent are supplied to a first of the reaction stages in relative amounts to provide a first mole ratio of aromatic substrate to alkylating agent. The effluent from the first reaction zone is supplied to a second reaction stage. Alkylating agent is separately supplied to the second reaction stage in an amount to provide a mole ratio of the aromatic substrate to the alkylating agent which is less than corresponding ratio of these reactants as supplied to the first recited alkylation stage.

10 Claims, 1 Drawing Sheet

5,196,623

AROMATIC ALKYLATION PROCESS EMPLOYING ZEOLITE OMEGA CATALYST

RELATED APPLICATION

This application is a continuation-in-part of copending application Ser. No. 371,502, filed Jun. 23, 1989, now U.S. Pat. No. 5,073,653.

TECHNICAL FIELD OF THE INVENTION

This invention relates to the alkylation of aromatic compounds and more particularly to the alkylation of an aromatic substrate in the liquid phase by a low molecular weight alkylating agent over an alkylation catalyst comprising zeolite omega and in a plurality of reaction stages.

BACKGROUND OF THE INVENTION

Processes for the alkylation of aromatic feed stocks and the use of molecular sieves as catalysts in aromatic alkylation process are well known in the art. Such alkylation processes may be used to produce mono- or polyalkylated products ranging from low to high molecular weights and may be carried out in the vapor phase, in the liquid phase, or under intermediate conditions in which both liquid and vapor phases exist.

U.S. Pat. No. 4,185,040 to Ward et al. discloses an alkylation process employing a molecular sieve catalyst of low sodium content which is said to be especially useful in the production of ethylbenzene from benzene and ethylene, and cumene from benzene and propylene. Examples of suitable zeolites include molecular sieves of the X, Y, L, B, ZSM-5, and Omega crystal types, with steam stabilized hydrogen Y zeolite being preferred. The Ward alkylation process may be carried out with either upward or downward flow, the latter being preferred, and preferably under temperature and pressure conditions so that at least some liquid phase is present, at least until substantially all of the olefin alkylating agent is consumed. Ward states that rapid catalyst deactivation occurs under most alkylating conditions when no liquid phase is present.

Another alkylation procedure is disclosed in European Patent Application No. 272,830 to Ratcliffe et al. The Ratcliffe procedure employs molecular sieve alkylation catalysts which have been treated in a manner to improve selectivity to monoalkylation, specifically in the propylation of benzene to produce cumene. Selectivity is said to be increased by at least one percentage point by first depositing a carbonaceous material on the catalyst and then subjecting the resultant carbon containing catalyst particles to combustion. Specifically disclosed zeolitic crystalline molecular sieves include those selected from the group of Y zeolites, fluorided Y zeolites, X zeolites, zeolite beta, zeolite L and zeolite omega. A preferred zeolite is an ammonium exchanged and calcined Y zeolite.

As indicated above, one of the molecular sieve catalysts disclosed in the aforementioned patents to Ward et al. and Ratcliffe et al. is zeolite omega. Crystalline zeolite omega is identified by its characteristic x-ray defraction pattern, and basic procedures for its preparation are disclosed in U.S. Pat. No. 4,241,036 to Flanigan et al. Zeolite omega is described as being capable of absorbing relatively large molecules such as benzene and cyclic compounds, and as being capable of catalyzing various reactions including an alkylation reaction involving propylene and benzene. Flanigan discloses forming a slurry of 10 grams of decationized zeolite omega with 1 gram-mol of benzene and adding excess propylene at room temperature while stirring. A steady rise in temperature was taken as an indication that an exothermic alkylation reaction was occurring and a benzene conversion of 50.9% was obtained after one hour.

A stabilized and dealuminated omega zeolite, as well as a process for its preparation, is disclosed in U.S. Pat. No. 4,724,067, to Raatz et al. The modified omega zeolite is described a exhibiting catalytic activity in the cracking of heavy oil fractions. A preferred process for preparing the stabilized and dealuminated omega zeolite consists of 1) removing the organic cations incorporated during synthesis of the zeolite by roasting in air; 2) exchanging the alkali cations with ammonium cations; 3) calcining in the presence of steam; and 4) acid etching. After modification, the disclosed omega zeolite has a $SiO_2/Al_2O_3$ molar ratio higher than ten (10), and is further characterized by the presence of a particular lattice of secondary pores.

The use of molecular sieves to produce relatively high molecular weight alkyl benzenes which may be used as precursors in the production of alkylarylsulfonate detergents is disclosed in U.S. Pat. No. 4,301,316 to Young. In Young, relatively long chain length alkylating agents having one or more reactive alkyl groups of at least 5 carbon atoms are employed in the alkylation of benzene in the presence of a crystalline zeolite alkylation catalyst. The reactants may be in either the vapor phase or the liquid phase and the zeolite catalysts may be either modified or unmodified. Preferred zeolite catalysts include zeolite beta, ZSM-4, ZSM-20, ZSM-38, and synthetic and naturally occurring isotopes thereof such as zeolite Omega and others. As described in Young, the zeolites may be subject to various chemical treatments including alumina extraction and combination with one or more metal components such as the metals of groups IIB, III, IV, VI, VIIA and VIII. The zeolites may also be subjected to thermal treatments including steaming or calcination in air, hydrogen or an inert gas. Specifically disclosed in Young is the reaction of benzene and 1-dodecene over zeolite HZSM-4 in a flow reactor at 205° C. and 210 psig.

Aromatic alkylation reactions such as the alkylation of benzene with ethylene are highly exothermic reactions and as a result the alkylation reactions may be carried out in stages with intermediate cooling steps. For example, U.S. Pat. No. 4,107,224 to Dwyer, discloses the vapor phase ethylation of benzene over a zeolite catalyst in a down flow reactor with the intermediate injection of cold reactants in a diluent. Specifically disclosed is the interstage injection of ethylene and benzene. Dwyer characterizes the catalysts suitable for use in his invention in terms of those having a constraint index within the approximate range of from 1 to 12. Disclosed as examples of suitable zeolites, with the constraint index in parenthesis, are ZSM-5 (8.3), ZSM-11 (8.7), ZSM-12 (2), ZSM-35 (4.5), ZSM-38 (2) and similar materials. Other molecular sieves, including, ZSM-4 (constraint index 0.5), are disclosed as having constraint indices outside of the range suitable for use in the Dwyer ethylbenzene production process. ZSM-4 is identified in Dwyer (col.10) as "ZSM-4 (Omega)".

SUMMARY OF THE INVENTION

In accordance with the present invention, there is provided a new and advantageous process for the alkylation of aromatic substrates by relatively low molecular weight alkylating agents under moderate temperature conditions, including liquid phase conditions, employing an alkylation catalyst comprising zeolite omega. In carrying out the invention, a feedstock containing an aromatic substrate is supplied to a reaction zone and brought into contact with a $C_2$-$C_4$ alkylating agent in the presence of a zeolite omega alkylation catalyst. The resulting alkylaromatic substrate is then recovered from the reaction zone.

In one embodiment of the invention, a plurality of series connected reaction stages containing the zeolite omega catalyst are utilized. When liquid phase conditions are desired, the reaction stages are operated at an average temperature of no more than 300° C. with the interstage injection of the $C_2$-$C_4$ alkylating agent in a manner to maintain at least 1 mole percent of alkylating agent solubilized in the aromatic substrate. Preferably at least 2 mole percent alkylating agent is solubilized in the aromatic substrate.

A preferred application of the present invention is in the alkylation of benzene with ethylene to produce ethylbenzene. This process is preferably carried out in the liquid phase over a zeolite omega catalyst, and under alkylation conditions under which the xylene make, based upon the amount of ethylbenzene produced, is no more than 0.05 wt.%.

Another embodiment of the present invention involves the use of zeolite omega in a process for the liquid phase alkylation of an aromatic substrate with a $C_2$-$C_4$ alkylating agent in a multi-stage reaction system in which the aromatic substrate/alkylating agent mole ratio is progressively increased when going from one stage to another. In this aspect of the invention, the reaction stages containing the omega catalyst preferably are operated under temperature and pressure conditions effective to cause alkylation of the aromatic substrate, with the pressure being above the vapor pressure of the aromatic substrate and below the vapor pressure of the alkylating agent at the alkylation reaction conditions. A feedstock comprising the aromatic substrate and the alkylating agent is supplied to a first of the reaction stages in relative mounts to provide a first mole ratio of aromatic substrate to alkylating agent. Effluent comprising a mixture of the aromatic substrate and alkylated product is withdrawn from the first reaction stage and supplied to a second reaction stage. Alkylating agent is separately supplied to the second reaction stage in an amount to provide a mole ratio of the aromatic substrate to the alkylating agent which is less than corresponding ratio of reactants supplied to the first recited reaction stage. Preferably, the multistage reaction system in this embodiment of the invention comprises from 3-8 reaction stage and the interstage injection of alkylating agent is controlled so that a progressively decreasing mole ratio of aromatic substrate to alkylating agent, e.g., benzene/ethylene mole ratio, continues across the reaction system.

BRIEF DESCRIPTION OF THE DRAWING

The drawing (FIG. 1) is a schematic illustration of a specific embodiment for carrying out the invention employing a plurality of series connected reaction stages.

DETAILED DESCRIPTION

Figure 1:
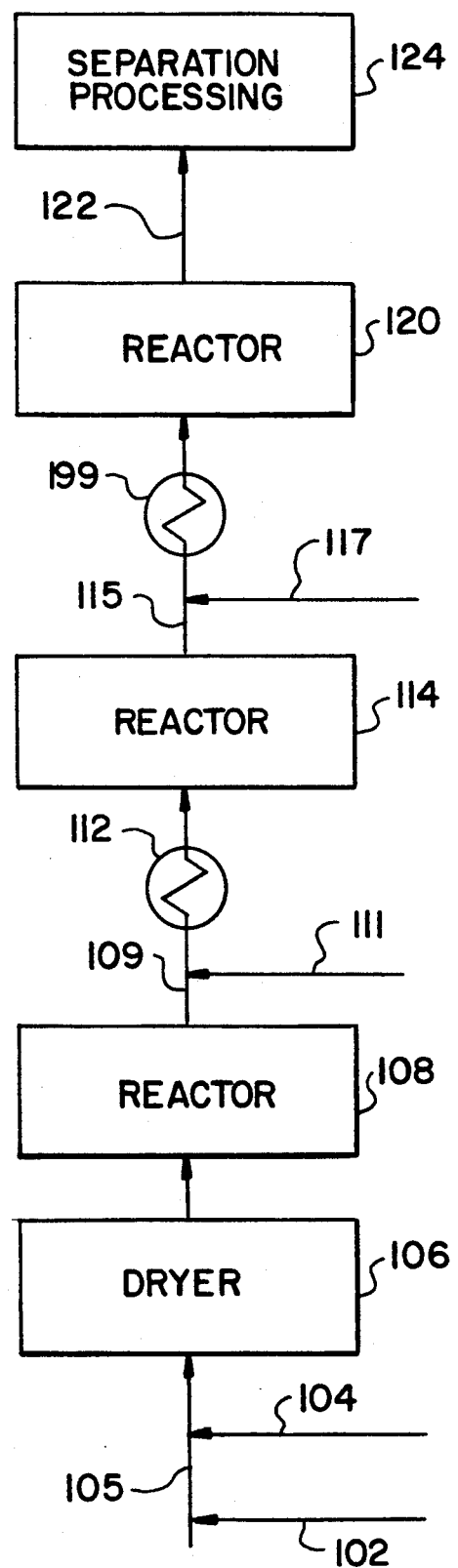

The present invention involves the use of an aromatic alkylation catalyst comprising zeolite omega under relatively mild liquid-phase alkylation conditions. The invention is especially applicable to the ethylation of benzene under mild liquid phase conditions producing low xylene make and the invention will be described specifically by reference to the production of ethylbenzene. However, other alkylation reactions may be utilized in carrying out the invention. For example, the invention may be applied to the reaction of propylene with benzene to produce cumene. Also, while olefinic alkylating agents normally will be employed, other alkylating agents such as alkynes, alkylhalides, alcohols, ethers, and esters as disclosed, for example, in U.S. Pat. No. 3,551,510 to Pollitzer et al. may be used. Other aromatic substrates, such as toluene and xylene, also may be subjected to alkylation in accordance with the invention.

The activity of zeolite omega as utilized in the present invention is in direct contrast to the teachings found in the aforementioned patent to Dwyer which suggests that ZSM-4 (Omega), because of its low constraint index, is unsuitable for use under the relatively severe conditions involved in the vapor phase ethylation of benzene, and in the aforementioned patent to Young, which limits its application to relatively long chain alkylating agents. Dwyer, which is directed to ethylbenzene production under relatively severe temperature conditions well above 300° C., (i.e., 650-900° F. and preferably 700-850° F.), teaches, as noted above, that ZSM-4 (Omega) cannot be used as a catalyst in the ethylation of an aromatic substrate, even under the high temperature conditions involved in the Dwyer process. The aforementioned patent to Flanigan, while recognizing that zeolite omega could be used as a catalyst in an exothermic alkylation reaction involving propylene and benzene, indicated that even after an hour of mixing, benzene conversion was only 51%, notwithstanding that benzene (and not propylene) was the limiting reactant, i.e., that an excess of propylene was used.

The present invention proceeds in a manner directly contrary to these prior art teachings. In the process of the present invention, zeolite omega is an effective catalyst for the alkylation of an aromatic substrate with a low molecular weight ($C_2$-$C_4$) alkylating agent. Moreover, it is an effective alkylating agent under mild liquid-phase conditions involving temperatures of 300° C. or less, providing high conversion efficiency and high selectivity to monoalkylation. As noted previously, these mild reaction conditions permit the production of ethylbenzene with a xylene content which is kept at a low level, less than 0.05 wt.% based upon ethylbenzene production.

Crystalline zeolite omega, as identified by its x-ray defraction pattern, and basic procedures for its preparation are disclosed in U.S. Pat. No. 4,241,036 to Flanigan et al. Zeolite omega is synthesized by the hydrothermal digestion of a reaction mixture comprising silica, alumina, and alkali or alkaline earth metal oxide or hydroxide, specifically sodium hydroxide, and an alkylammonium component, specifically tetramethylammonium hydroxide.

The chemical composition of zeolite omega in a preferred form may be characterized as follows:

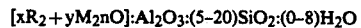

wherein:
 x has a value ranging from 0–0.7 and the sum of x and y ranges from 0.5–1.5

R represents hydrogen, ammonium, alkylammonium or mixtures thereof;

M is a metal compound, usually an alkali metal compound such as sodium;

n is the valance of M,

For a further description of zeolite omega and its preparation, reference is made to the aforementioned U.S. Pat. No. 4,241,036 to Flanigan et al., the entire disclosure of which is incorporated herein by reference.

In experimental work carried out respecting the invention a zeolite catalyst was employed in the liquid-phase reaction of ethylene and benzene to produce ethylbenzene. Although zeolite Y was employed as the catalyst in the experimental work presented herein, zeolite omega may also be employed, as well as other molecular sieves such as zeolite beta. The experimental work was carried out in an upflow flooded reactor heated by a sand bath set at a nominal temperature of 200° C. The reactor was equipped with four thermocouples spaced evenly from the inlet, TC #1, to the outlet, TC #4. The reactor contained 12.9 grams (26 ml) catalyst comprising 80 wt.% crystalline zeolite and 20 wt.% alumina binder. The benzene was supplied to the bottom of the reactor at a rate to provide a space velocity (LHSV) of about 8 $hr^{-1}$. Ethylene was supplied to provide a nominal benzene/ethylene mol ratio of about 5 although the actual mol ratio increased to about 10 during about 40-65 hours into the run and decreased back to about 5. The results of the experimental work are set forth in Table I. The effluent analysis is set forth in weight percent for benzene and ethylbenzene and for other components including the xylenes, toluene, cumene, metadiethylbenzene and ortho and para diethyl benzene, in yields relative to ethylbenzene.

below 0.03 wt.% based upon the ethylbenzene produced.

In carrying out the invention, the alkylation reaction is carried out at pressures well above the vapor pressure of the aromatic substrate at the reaction temperature involved in order to ensure that a liquid phase is retained in the reactor. In order to provide a complete liquid phase reaction, a flooded bed format is used in which the catalyst be is completely immersed in liquid. This can readily be accomplished using an up flow technique such as used in the experimental work and this usually will be preferred in carrying out the invention. However, downflow flooded bed operation can be accomplished by control of the outlet flow rate to ensure that the catalyst beds are covered by liquid benzene or other aromatic substrate.

Preferably a staged reaction format is employed in order to ensure good solubility of the ethylene (or other alkylating agent) in the benzene (or other aromatic substrate) and provide that the entire reaction takes place in the liquid phase. In addition, use of multiple stages provides an opportunity for interstage cooling where adiabatic reactors are used or permits the use of several isothermal reaction stages.

Turning now to the drawing, there is shown a schematic illustration of a staged reactor system used for the production of ethylbenzene by the reaction of ethylene with benzene which includes a plurality of adiabatic reactors with interstage cooling and injection of ethylene. More particularly and as illustrated in the drawing ethylene and benzene are supplied via lines 2 and 4 to the inlet line 5 of a dehydration unit 6. The dehydration unit functions to dehydrate the input to the alkylation reactors so that it is essentially dry, desirably containing

TABLE I

| SAMPLE NO. 1 | 1 | 2 | 3 | 4 | 5 | 6 | 7 | 8 | 9 |
|---|---|---|---|---|---|---|---|---|---|
| Cat Age Hours | 11.1 | 17.3 | 27.9 | 41.3 | 49.0 | 65.3 | 73.1 | 89.7 | 161.8 |
| Press. PSI | 305 | 340 | 300 | 250-330 | 250-300 | 260-215 | 450-510 | 475-530 | 505-544 |
| Outlet TC 4 | 224 | 217 | 217 | 211 | 210 | 209 | 215 | 214 | 206 |
| TC 3 | 222 | 219 | 216 | 211 | 211 | 209 | 216 | 214 | 206 |
| TC 2 | 206 | 206 | 205 | 204 | 204 | 203 | 207 | 206 | 203 |
| Inlet TC 1 | 200 | 200 | 200 | 199 | 200 | 200 | 201 | 200 | 201 |
| BZ Wt % | 82.78 | 86.28 | 87.99 | 88.25 | 90.61 | 91.16 | 87.17 | 95.20 | 95.43 |
| EB WT % | 15.001 | 11.587 | 19.060 | 10.331 | 8.360 | 7.783 | 10.432 | 3.727 | 3.488 |
| YIELDS RELATIVE TO EB | | | | | | | | | |
| N-AR WT % | 0.783 | 1.104 | 1.819 | 1.571 | 1.300 | 2.390 | 1.838 | 3.370 | 7.085 |
| TOL PPM | 1147 | 863 | 775 | 1229 | 1232 | 1259 | 968 | 1100 | 4100 |
| P-X PPM | 0 | 0 | 0 | 0 | 0 | 0 | 0 | 0 | 0 |
| M-X PPM | 180 | 164 | 129 | 0 | 0 | 0 | 134 | 188 | 0 |
| O-X PPM | 13 | 17 | 0 | 0 | 0 | 0 | 29 | 27 | 0 |
| CUM PPM | 960 | 1519 | 1272 | 542 | 622 | 591 | 3892 | 7299 | 10895 |
| M-DEB WT % | 6.956 | 7.808 | 7.762 | 5.665 | 5.233 | 5.413 | 7.720 | 6.818 | 2.097 |
| O + P-DEB WT % | 5.365 | 8.326 | 8.668 | 5.236 | 5.123 | 5.043 | 10.777 | 13.532 | 5.941 |
| TOTAL XYLENES | 193.320 | 181.241 | 129.225 | 0.000 | 0.000 | 0.000 | 162.960 | 214.667 | 0.000 |
| TOTAL DEB | 12.321 | 16.134 | 16.430 | 10.900 | 0.356 | 0.456 | 18.498 | 20.350 | 7.948 |

As can be seen from an examination of the experimental data presented in Table I, and bearing in mind that, for the most part, the ethylene charge to the reactor was about 20% of the stoichiometrically equivalent amount of benzene (about 10% during a portion of the run), it can be seen that the zeolite catalyst is highly active and shows good selectivity to ethylbenzene production. The activity of the catalyst remained good over much of the run. The low ethylbenzene production occurring at the last two data points in Table I are thought to be an experimental aberration, possibly because all of the ethylene was not dissolved in the benzene. The xylene production was low and through out the run and stayed less than 100 ppm water and more preferably less than 50 ppm water. By way of example, dehydrator 6 may take the form of a packed column packed with a desiccant such as silica gel or other suitable hydroscopic medium.

The dehydrator effluent is supplied to a reactor 8, the first of a plurality of series connected alkylation reactors operated in an upflow mode. Reactor 8 is operated at an average temperature of 300° C. or less and preferably at an average temperature within the range of 200°-250° C. The pressure on a reactor 8 is sufficient to maintain the benzene in the liquid phase and preferably is at least 50 psi above the vapor pressure of the benzene at the reactor temperature. Typically the reactor pressure is within the range of about 500-600 psia. The remaining downstream reactors normally are operated under approximately the same conditions as the initial reactor. The effluent from the initial reactor 8 is withdrawn via line 9 and applied through a heat exchanger 12 where it is cooled prior to being supplied to the second stage reactor 14. Ethylene is supplied via line 11 where it is mixed with the effluent from the first reactor 8. Preferably the ethylene is supplied to the reactor effluent prior to cooling as shown in the drawing in order to facilitate distribution of the ethylene throughout the liquid benzene. Desirably, the cooling step is carried out to reduce the temperature of the feed mixture supplied to the second reactor 14 to a value about the same as the inlet temperature to the first reactor 8. The average temperature in the second reactor normally will be about the same as that of the first reactor. The pressure will of necessity be somewhat lower in order to provide for sufficient pressure gradient to accommodate flow through the system. The effluent from the second reactor 14 is supplied along with ethylene provided via line 17 to a second interstage cooling unit 19 where the charge mixture to third reactor 20 is again cooled to a temperature about equal to the inlet temperature for the first two reactors.

The output from reactor 20 is supplied via line 22 to a down-stream separation and processing unit 24. In The amount of ethylene solubilized in the benzene charge to each reactor stage will depend in part upon the number of reactor stages employed. Preferably at least 3 reactor stages, as illustrated, will be used. Additional reactor stages will be provided although the total number of stages normally will not exceed 8. Preferably the pressure in each reaction stage and the amount of ethylene supplied therein is such as to provide at least 1 mole percent of ethylene solubilized in the benzene. Usually at least 2 mole percent of ethylene will be solubilized in the charge to each reactor. Preferably, unless a great many reactor stages are employed, usually the amount of ethylene solubilized in the liquid benzene phase of each reactor will be at least 4 mole percent.

The following Table II gives exemplary conditions and reaction parameters for a multistage system of the type shown in the drawing but employing five reaction stages. As will be discussed below, Table II also illustrates a preferred mode of operation when going from one reaction stage to the next as well as the advantages accruing in the use of multiple reaction stages in a liquid phase alkylation process. In carrying out this embodiment of the invention, zeolite omega may be employed. However, other catalysts which are suitable for liquid phase alkylation may also be used. Examples of such catalysts include molecular sieves such as zeolite beta and zeolite Y.

TABLE II

| Reaction Stage | Temp C | | Press (Psia) | | Benzene Feed Rate Moles | Benz Conv % | $C_2H_4$ Feed Rate Mole | BZ $C_2H_4$ |
|---|---|---|---|---|---|---|---|---|
| | In | Out | In | Out | | | | |
| 1 | 210 | 240 | 500 | 485 | 4 | 9% | .4 | 10.0 |
| 2 | 210 | 240 | 480 | 465 | 3.64 | 10% | .4 | 9.1 |
| 3 | 210 | 240 | 460 | 445 | 3.28 | 11% | .4 | 8.2 |
| 4 | 210 | 240 | 440 | 425 | 2.97 | 12% | .4 | 7.3 |
| 5 | 210 | 240 | 420 | 415 | 2.56 | 14% | .4 | 6.4 | unit 24, ethylbenzene is separated and withdrawn as the product of the alkylation plant. Typically ethylbenzene will be used a the charge to a dehydrogenation system where it undergoes catalytic dehydrogenation in the production of styrene. Normally benzene and ethylene will be separated in unit 24 and recycled for use in the alkylation process. Heavier polyethylbenzenes may be transalkylated with benzene to produce additional ethylbenzene.

As is conventional, a stoichometric excess of benzene to ethylene will be supplied in the charge stock to the alkylation reactors in order to enhance selectivity for monoalkylation. Operation of the reactors to provide liquid phase alkylation under relatively mild conditions not only minimizes the xylene produced in the alkylation reaction but also enables the use of a somewhat lower benzene/ethylene molar ratio than is usually the case. Usually the benzene/ethylene molar ratio will be 5:1 or less and more preferably 4:1 or less. Benzene/ethylene molar ratios as low as about 2:1 may be employed. Ratios greater than 5:1 can be used. However, there is usually little incentive to use extremely high ratios and as a practical matter the benzene/ethylene molar ratio will seldom exceed 15:1. The benzene/ethylene mole ratios referred to above are with respect to the overall system and for a multi-stage reaction system such as depicted in the drawing, the benzene/ethylene ratio of the feed to each stage will be less than the overall ratio.

In Table II, the idealized reactor conditions for the ethylation of benzene with ethylene are illustrated in columns 2-5. The benzene feed rate in moles per unit time to each of the reaction stages is set forth in column 6. Benzene conversion for each reaction stage is indicated in column 7 and the ethylene feed rate in moles per unit time to each reaction zone is set forth in column 8. The last column presents the mole ratio of benzene to ethylene at the input of each of the successive reaction stages. The data presented in Table I is based upon the idealized case, assuming that benzene conversion is about 90% of theoretical based upon the feed rate of ethylene which, of course, is the limiting reactant.

At the temperature and pressure conditions depicted in Table I, the solubility of ethylene in the liquid aromatic compounds involved, including benzene, ethylbenzene and polyethylbenzene, is about 10 mole %. The ethylene feed to the first reaction stage is controlled in order to provide an amount of ethylene near the solubility limit. Within the first reaction zone, 0.36 moles of benzene are converted and the effluent from the first reaction zone, after cooling as described previously, is applied to the second reaction zone. The aromatic feed to the second reaction zone will comprise about 3.64 moles of benzene and about 0.36 moles of ethylbenzene and polyethylbenzenes per unit time. Since the ethylated product can serve to solubilize the ethylene at the reaction conditions, the ethylene feed rate can be retained at 0.4 moles per unit time, resulting in a decreased benzene/ethylene mole ratio and an increased benzene conversion rate. The relationships described above prevail when going from one reaction stage to the next, resulting in a decreased mole ratio of benzene to ethylene in each succeeding reaction stage and an increased benzene conversion rate. Although in the idealized case presented in Table I, the interstage injection of ethylene is maintained constant. This need not necessarily be the case. For example, the ethylene feed rate can be increased or decreased slightly from one stage to the next, or alternatively decreased and increased, so long as the overall progression across the multistage system is one of decreasing benzene/ethylene ratio with the attendant increase in benzene conversion. By way of an example of a progressively decreasing feed rate and with reference to the system depicted in Table II, the ethylene feed rate can be progressively decreased by 2-3% when going from one reaction stage to the next while retaining the characteristic of a decreasing benzene/ethylene ratio as depicted in the Table. If the ethylene feed rate is increased when going from one stage to the next, it is preferred to maintain the ethylene below the solubility limit at the temperature and pressure conditions involved in order to avoid multiphase flow through the catalyst bed.

Multistage ethylation of benzene may also be carried out in accordance with the present invention employing isothermal reaction zones. Isothermal reactors can take the form of shell and tube type heat exchangers with the alkylation catalyst deposited within the tubes and with a heat transfer medium circulated through the shell surrounding the catalyst filled tubes. The heat exchange medium will of course be supplied through the reactors at rates to maintain a relatively constant temperature across each reaction stage. In this case interstage cooling will be unnecessary although it will be preferred to inject ethylene at the front of each reaction stage.

Having described specific embodiments of the present invention, it will be understood that modification thereof may be suggested to those skilled in the art, and it is intended to cover all such modifications as fall within the scope of the appended claims.

I claim:

1. In a process for the production of ethylbenzene by the liquid phase ethylation of benzene, the steps comprising:

(a) supplying a benzene feedstock into a reaction system containing an alkylation catalyst comprising zeolite omega;
   (b) supplying an ethylating agent to said reaction system;
   (c) operating said reaction system at temperature and pressure conditions providing a pressure in said reaction zone at least 50 psi above the vapor pressure of said benzene and causing mono-ethylation of said benzene in the liquid phase by said ethylating agent in the presence of said catalyst, and under which conditions the xylene made based upon the amount of ethylbenzene produced is no more than 0.05 wt.%; and
   (d) recovering ethylbenzene from said reaction system.

2. The process of claim 1, wherein said reaction system comprises a plurality of series connected reaction stages containing said zeolite omega alkylation catalyst, supplying said benzene feedstock to the first of said series connected reaction stages and passing the effluent from said first reaction stage to at least a second of said reaction stages and separately supplying said ethylating agent to each of said reaction stages.

3. The process of claim 2, wherein said ethylating agent is ethylene.

4. The process of claim 3, further comprising the step of cooling the effluent from said first reaction stage prior to supplying said effluent to said second reaction stage.

5. The process of claim 4, wherein the ethylene supplied to said second reaction stage is mixed with the effluent from said first reaction stage prior to said cooling step.

6. The process of claim 3, comprising at least three reaction stages containing said zeolite omega alkylation catalyst.

7. The process of claim 6, wherein said reaction stages are carried out in adiabatic reaction zones.

8. The process of claim 7, further comprising the step of cooling the effluent from each of the first and second of said reaction stages prior to applying said effluent to the next succeeding reaction stage.

9. The process of claim 8, wherein the ethylene supplied to said succeeding reaction stages is mixed with the effluent from the preceding reaction stage prior to said cooling step.

10. The process of claim 3, wherein said reaction stages are carried out in isothermal reaction zones.

* * * * *